United States Patent [19]
Vollhardt

[11] Patent Number: 5,981,792
[45] Date of Patent: Nov. 9, 1999

[54] PROCESS FOR THE PRODUCTION OF 1-FUNCTIONAL ALLYLALCOHOL CARBOXYLIC ESTERS

[75] Inventor: Jürgen Vollhardt, Bevern, Germany

[73] Assignee: Dragoco Gerberding & Co. AG, Germany

[21] Appl. No.: 09/031,131

[22] Filed: Feb. 26, 1998

[30] Foreign Application Priority Data

Feb. 27, 1997 [DE] Germany .............................. 197 07 959

[51] Int. Cl.$^6$ ............................ C07C 67/00; C07C 69/76; C07C 67/02
[52] U.S. Cl. ......................... 560/239; 560/106; 560/113; 560/254
[58] Field of Search ..................... 560/106, 113, 560/239, 254

[56] References Cited

U.S. PATENT DOCUMENTS

| | | | |
|---|---|---|---|
| 3,975,310 | 8/1976 | Kovats et al. | 512/13 |
| 4,169,109 | 9/1979 | Yoshida et al. | 568/313 |
| 5,614,484 | 3/1997 | Panandiker | 510/102 |
| 5,756,827 | 5/1998 | Sivik | 560/201 |

OTHER PUBLICATIONS

G. V. Kryshtal et al., Izvestiya Akademii Nauk SSSR, Seriya Khimicheskaya, No. 3, pp. 679–681, Mar. 1987.

*Primary Examiner*—Samuel Barts
*Assistant Examiner*—Rosalynd Keys
*Attorney, Agent, or Firm*—Pendorf & Cutliff

[57] ABSTRACT

The process for preparing 1-functional allyl alcohol carboxylic esters comprises reacting a 3-functional allyl alcohol with the anhydride of the carboxylic acid at temperatures above 100° C. in the presence of metal compounds of transition groups V to VII, namely at temperatures of 100–200° C., preferably 130–150° C. As metal compounds, it is possible to use oxidic metal compounds in the highest or at least second highest oxidation state of the transition metals, for example tungstic acid or its salts and/or tungsten (VI) oxide and/or molybdenum(V) oxide and/or molybdenum(VI) oxide and/or rhenium(VII) oxide. The 3-functional allyl alcohol and the carboxylic anhydride are advantageously used in equimolar amounts, if desired with a slight excess of anhydride, and an alkali metal salt of a weak acid, for example sodium carbonate or sodium acetate, can be added to the reaction mixture in an amount sufficient to trap free protons.

8 Claims, No Drawings

PROCESS FOR THE PRODUCTION OF 1-FUNCTIONAL ALLYLALCOHOL CARBOXYLIC ESTERS

BACKGROUND OF THE INVENTION

Field of the Invention

The group of 1-functional allyl alcohol carboxylic esters encompasses economically important compounds which are either useful as such or can be reacted to form further economically important compounds, for example they can be saponified to form the corresponding 1-functional allyl alcohols.

It is known that 1-functional allyl alcohol carboxylic esters of the general formula 2 can be obtained according to the following scheme involving a 3,1-allyl rearrangement

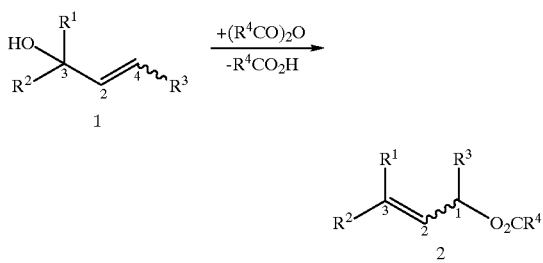

$R^1$ and $R^3$=H, alkyl or aryl
$R^2$=any radical, but not H
$R^4$=alkyl or aryl by reacting 3-functional secondary or tertiary allyl alcohols of the general formula 1 with carboxylic anhydrides. The 3-functional allyl alcohols of the general formula 1 are in turn obtainable by addition of vinyl or acetylene metal compounds onto carbonyl compounds.

However, this rearrangement reaction in which an esterification of the rearranged alcohol function takes place simultaneously has hitherto proceeded in a quite unsatisfactory manner, particularly in respect of the yields achieved. In a typical example, it is carried out under strongly acidic conditions in a solvent mixture of acetic acid, acetic anhydride and p-toluenesulphonic acid, with the acetates of the rearranged allyl alcohols being obtained. However, this results in undesired secondary reactions such as eliminations or cyclizations which greatly reduce the yield of the desired rearranged product. Thus, when using, for example, linalool mainly cyclizations are observed, while the desired products geranyl acetate and neryl acetate are formed only as by-products.

SUMMARY OF THE INVENTION

It is an object of the invention to improve the process so that considerably improved yields are obtained at little expense. This object is achieved by the 3-functional allyl alcohol being reacted with the anhydride of the carboxylic acid at a temperature above 100° C. preferably between 100° C. and 200° C., in the presence of a compound or a plurality of compounds of a metal or a plurality of metals of transition groups V to VII. It has surprisingly been found that this enables a yield of more than 70%, usually up to about 80%, of the allyl alcohol carboxylic ester of the general formula 2 to be achieved in about 1–5 h.

DETAILED DESCRIPTION OF THE INVENTION

The use of transition metal catalysts in the allyl rearrangement is known per se. Thus, according to Chabardes, 3-functional allyl alcohols are reacted at elevated temperatures in the presence of vanadium(V) compounds to give the isomeric 1-functional allyl alcohols and, according to Hosogai, a similar reaction occurs in the presence of tungstic esters. However, in both cases there is no formation of the 1-functional allyl alcohol carboxylic ester, but instead only the 1-functional alcohol which is in equilibrium with the 3-functional alcohol. The position of the equilibrium is generally on the starting material side, i.e. on the side of the higher-substituted alcohol. In the rearrangement of linalool, for example, only about 30–40% of geraniol and nerol are formed as a mixture. Furthermore, the reaction product cannot be removed from the reaction mixture by distillation in order to achieve complete conversion if it, like geraniol/nerol, has a higher boiling point than the starting material. The reaction therefore reaches a final yield of only about 30–40% and then has to be stopped. In view of this, it could not have been foreseen that the reaction procedure of the invention gives yields which are easily twice as high.

The metal compounds used are preferably the oxides and hydroxides (metalic acids) of the transition metals in the highest or second highest oxidation state. Lower oxidation states are not ruled out in principle, but generally lead to lower yields. Good results are achieved using tungstic acid or its salts and/or tungsten(VI) oxide and/or molybdenum (V) oxide and/or molybdenum(VI) oxide and/or rhenium (VII) oxide. Among the group of metal compounds mentioned, the tungsten compounds stand out since when they are used the reaction proceeds either more quickly or more selectively in terms of undesired oxidation/secondary reactions than when using (only) the other metal compounds mentioned.

It is advantageous also to add to the reaction mixture an amount of an alkali metal salt of a weak acid, e.g. sodium carbonate or sodium acetate, which is sufficient to ensure that the concentration of free protons in the reaction mixture is very low. When using a free metallic acid, the addition of such a salt is very necessary, but is also advisable when using other metal compounds such as oxides or salts of the metallic acids.

The 3-functional allyl alcohol and the carboxylic anhydride should be used in at least equimolar amounts, with preference being given to a small excess of anhydride for reasons of reaction kinetics. It is also possible to use a deficiency of anhydride, but the reaction is then not complete and the yields are reduced accordingly.

The following examples illustrate the invention:

EXAMPLE 1

Reaction of Linalool with Acetic Anhydride and Tungstic Acid/Sodium Acetate 770 g (5.0 mol) of linalool are added dropwise at 130–140° C. to a mixture of 561 g of acetic anhydride (5.5 mol), 7.5 g of sodium acetate (91.5 mmol) and 2.0 g of tungstic acid (8.0 mmol). After a total of 2 hours, water is added at 80° C. Two phases are formed and these are separated from one another. The organic phase is washed twice with water. This gives 870 g of a yellowish oil containing about 50% of geranyl acetate and about 25% of neryl acetate as well as about 1.5% of terpineol acetate (analysis by gas chromatography).

EXAMPLE 2

Reaction of Linalool with Benzoic Anhydride and Tungstic Acid/Sodium Carbonate 70 g (0.45 mol) of linalool are added dropwise at 130–140° C. to a mixture of 113 g of benzoic anhydride (0.5 mol), 1.0 g of sodium carbonate (9.4 mmol) and 1.1 g of tungstic acid (4.4 mmol). After a total of 4.5 hours, water and toluene are added at 80° C. Two phases are formed and these are separated from one another. The organic phase is washed with water and soda solution. The solvent is distilled off. This gives 110 g of a yellowish solid containing about 53% of geranyl benzoate and about 30% of neryl benzoate (analysis by gas chromatography).

EXAMPLE 3

Reaction of 6,7-dihydrolinalool with Acetic Anhydride and Tungstic Acid/Sodium Acetate 39 g (0.25 mol) of 6,7-dihydrolinalool are added dropwise at 130–140° C. to a mixture of 29 g of acetic anhydride (0.28 mol), 0.3 g of sodium acetate (3.6 mmol) and 0.1 g of tungstic acid (0.4 mmol). After a total of 1 hour, water and toluene are added at 80° C. Two phases are formed and these are separated from one another. The organic phase is washed with water. The solvent is distilled off. This gives 48 g of a yellowish oil containing about 54% of dihydrogeranyl acetate and about 28% of dihydroneryl acetate (analysis by gas chromatography).

EXAMPLE 4

Reaction of Linalool with Acetic Anhydride and Molybdenum(VI) Oxide/Sodium Acetate 13.8 g (90 mmol) of linalool are added dropwise at 130–140° C. to a mixture of 12 g of acetic anhydride (118 mmol), 0.5 g of sodium acetate (6.1 mmol) and 0.1 g of molybdenum(VI) oxide (0.69 mmol). After a total of 2.5 hours, water is added at 80° C. Two phases are formed and these are separated from one another. The organic phase is washed twice with water. About 20 g of a yellowish oil can be isolated. According to analysis by gas chromatography, 72% of the linalool has been converted into a mixture of geranyl acetate and neryl acetate.

EXAMPLE 5

Reaction of Linalool with Acetic Anhydride and Rhenium(VII) Oxide/Sodium Acetate 13.8 g (90 mmol) of linalool are added dropwise at 130–140° C. to a mixture of 12 g of acetic anhydride (118 mmol), 0.5 g of sodium acetate (6.1 mmol) and 0.1 g of rhenium(VII) oxide (0.2 mmol). After a total of 1 hour, water is added at 80° C. Two phases are formed and these are separated from one another. The organic phase is washed twice with water. About 20 g of a yellowish oil can be isolated. According to analysis by gas chromatography, 82% of the linalool has been converted into a mixture of geranyl acetate and neryl acetate.

EXAMPLE 6

Reaction of 1-octen-3-ol with Acetic Anhydride and Tungstic Acid 128 g (1 mol) of 1-octen-3-ol are added dropwise at 130–140° C. to a mixture of 112.2 g of acetic anhydride (1.1 mol), 6.6 g of sodium acetate (80 mmol) and 2.5 g of tungstic acid (10 mmol). After a total of 1 hour, water is added at 80° C. Two phases are formed and these are separated from one another. The organic phase is washed twice with water. About 140 g of a yellowish oil can be isolated. According to analysis by gas chromatography, 75% of the 1-octen-3-ol has been converted into 2-octen-1-yl acetate.

What is claimed is:

1. A process for preparing a 1-functional allyl alcohol carboxylic ester of the general formula 2:

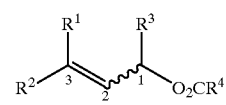

2 wherein $R^1$ and $R^3$=H, alkyl or aryl $R^2$=radical, but not H $R^4$=alkyl or aryl, wherein a 3-functional allyl alcohol of the general formula 1:

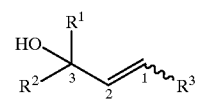

1 wherein $R^1$ and $R^3$=H, alkyl or aryl, and $R^2$=radical, but not H, is reacted with an anhydride of a carboxylic acid in the presence of one or more compounds of one or more metals of group V to VII at a temperature above 100° C.

2. A process according to claim 1, wherein the reaction is carried out at a temperature of 100 to 200° C.

3. A process according to claim 1, wherein one or more oxidizing metal compounds are used.

4. A process according to claim 1, wherein one or more of the metals of groups V to VII lie in the highest or second highest periods.

5. A process according to claim 1, wherein tungstic acid or its salts and/or tungsten (VI) oxide and/or molybdenum (V) oxide and/or molybdenum (VI) oxide and/or rhenium (VII) oxide is used.

6. A process according to claim 1, wherein the carboxylic acid anhydride and the 3-functional allyl alcohol are in equimolar mixtures or the carboxylic acid anhydride is in slight molar excess over the 3-functional allyl alcohol.

7. A process according to claim 1, wherein the reaction mixture is one which is a free proton generating mixture of an alkali salt of a weak acid, such as sodium carbonate or sodium acetate.

8. A process according to claim 1, wherein the reaction is carried out at a temperature of 130 to 150° C.

* * * * *